(12) United States Patent
Šmahovský et al.

(10) Patent No.: US 6,229,021 B1
(45) Date of Patent: May 8, 2001

(54) METHOD OF OMEPRAZOLE PREPARATION

(75) Inventors: Vendel Šmahovský, Pezinok; Vladimir Oremus, Bratislava; Katarina Heleyová, Žilina; Pavol Zlatoidský; Ondřej Gattnar, both of Bratislava; Ivan Varga, Hlohovec; Valdemar Štalmach, Bratislava; Ladislav Ježek, Modra, all of (SK)

(73) Assignee: Slovakofarma, A.S. (SK)

( * ) Notice: Subject to any disclaimer, the term of this patent is extended or adjusted under 35 U.S.C. 154(b) by 0 days.

(21) Appl. No.: 09/254,414

(22) PCT Filed: Sep. 8, 1997

(86) PCT No.: PCT/SK97/00008

§ 371 Date: Mar. 5, 1999

§ 102(e) Date: Mar. 5, 1999

(87) PCT Pub. No.: WO98/09962

PCT Pub. Date: Mar. 12, 1998

(30) Foreign Application Priority Data

Sep. 9, 1996 (SK) ........................................ 1155-96

(51) Int. Cl.⁷ ................................. C07D 403/02

(52) U.S. Cl. ............................................. 548/306.1
(58) Field of Search ........................... 548/306.1

(56) References Cited

U.S. PATENT DOCUMENTS 5,391,752 * 2/1995 Hoerrner et al. ..................... 546/271

FOREIGN PATENT DOCUMENTS

| 298 440 A1 | 7/1988 | (EP) . |
| 0 533 264 A1 | 3/1993 | (EP) . |
| WO 91/18895 | 12/1991 | (WO) . |
| WO 97/22603 | 6/1997 | (WO) . |

* cited by examiner

Primary Examiner—Joseph K. McKane
Assistant Examiner—Joseph Murray
(74) Attorney, Agent, or Firm—Zarley, McKee, Thomte, Voorhees & Sease

(57) ABSTRACT

The invention involves a method of preparation of omeprazole by a reaction of 5-methoxy-2-[(4-methoxy-3,5-dimethyl-2-pyridinyl)-methylthio]-1H-benzimidazole with peroxyacetic acid in a two-phase water and chlorinated organic solvent medium, in alkaline pH, subsequent separation of water and organic phases after the reaction and isolation of omeprazole from organic phase.

9 Claims, No Drawings

METHOD OF OMEPRAZOLE PREPARATION

This application is a 371 of PCT/SK97/00008 filed Sep. 8, 1997.

TECHNICAL FIELD

The invention solves a method of preparation of a pharmaceutical substance 5-methoxy-2-[(4-methoxy-3,5-dimethyl-2-pyridinyl)-methyl]sulphinyl]-1H-benzimidazole, which is known under its generic name omeprazole.

DESCRIPTION OF THE RELATED ART

According to the Swedish patent SE 4231, omeprazole is prepared by oxidation of 5-methoxy-2-[(4-methoxy-3,5-dimethyl-2-pyridinyl)-methylthio]-1H benzimidazole, (further referred to as the compound I) with m-chloroperoxybenzoic acid.

In the PCT application published under WO 91/118895 is described an improved method of preparation of omeprazole by oxidation of the compound I again with m-chloroperoxybenzoic acid, but in an alkaline medium.

Also other patents provide for preparation of omeprazole by oxidation of the compound I with different oxidizing agents.

In the European patent EP 484 265 preparation of omeprazole by oxidation of the compound I with hydrogen peroxide in the presence of molybdenum salts as catalysts is described.

The European patent EP 302 720 has patented preparation of omeprazole by oxidation of the compound I with hydrogen peroxide using vanadium catalysts. The British patent GB 2 239 453 describes preparation of omeprazole by photo-chemic oxidation of the compound I.

Other way of omeprazole preparation is oxidation of the compound I by magnesium peroxyphatalate provided for in the European patent EP 533 264, and oxidation by iodosobenzene or iodosotoluene described in the Spanish patent ES 539 793. The Spanish patent ES 543 816 describes preparation of omeprazole by oxidation of the compound I with m-chloroperoxybenzoic acid powder.

Disadvantages of these preparation methods are that prepared omeprazole is contaminated by starting substance and there are many side products produced during the reactions, including especially 5-methoxy-2-[[(4-methoxy-3,5-dimethyl -2-pyridinyl)-methyl]sulphonyl]-1H-benzimidazole as a product of following omeprazole oxidation.

The procedures mentioned above utilize relatively expensive oxidizing reagents.

The possible using of peroxyacetic acid in the preparation of compounds of this type is only generally mentioned, together with many other oxidizing agents (see, e.g. Houben-Weyl Vol. E11/Part 1, p. 702–752, EP 533 264, EP 298 440 . . . ).

The most frequently described oxidizing reagent in the preparation of omeprazole from the compound I is m-chloroperoxybenzoic acid.

The object of the present invention is the use of peroxyacetic acid as an oxidizing agent in the preparation of omeprazole from the compound I. Surprisingly, we have found, that the use of peroxyacetic acid as an oxidizing agent instead of m-chloroperoxybenzoic acid in the preparation of omeprazole provides a crude product of unexpectedly high purity. Practically, the product is not contaminated by hardly removable sulphone impurity, 5-methoxy-2-[[(4-metoxy-3,5-dimethyl-2-pyridinyl)-methyl]sulphonyl]-1H-benzimidazole, as in the case of omeprazole preparation by means of m-chloroperoxybenzoic acid.

The object of the present invention is to provide a method for the preparation of omeprazole, which utilizes a very cheap oxidizing agent. Furthermore, a such method for preparation of omeprazole is provided, in which neither toxic components nor components requiring expensive liquidation are formed, as in the case of other oxidizing reagents described in connection with the preparation of omeprazole (e.g. m-chloroperoxybenzoic acid, molybdenum and vanadium catalysts, magnesium peroxyphthalate, iodosobenzene and iodosotoluene).

When the reaction is completed, omeprazole is simply isolated from the organic phase, and acetic acid formed from the oxidizing agent remains in the aqueous phase and is liquidated in very easy and cheap way.

SUMMARY OF THE INVENTION

The mentioned disadvantages of the presently known methods for the omeprazole preparation are eliminated by a method of preparation of omeprazole according to the present invention, which comprises the reaction of 5-methoxy-2-[(4-methoxy-3,5-dimethyl-2-pyridinyl)-methylthio]-1H-benzimidazole (the compound I) with peroxyacetic acid in a two-phase water and chlorinated organic solvent medium, in alkaline pH, subsequent separation of water and organic phases after the reaction and isolation of omeprazole from organic phase.

The peroxyacetic acid is used in amount of 0,8 to 2,0 molar equivalents to the compound I, advantageously in the amount of 0,9 to 1,1 molar equivalent.

The pH of reaction mixture during the reaction is maintained from 7,1 to 9,5. The best is, however, to work with the pH ranging from 8,0 to 8,5.

The temperature of reaction mixture is maintained during the reaction from 0° C. to 25° C., the best range from 1° C. to 5° C.

As chlorinated organic solvent can be used dichloromethane, chloroform, or dichloroethane, using of dichloromethane is preferable.

When the reaction is completed, organic and water phases are separated, and omeprazole is isolated from the organic phase.

The advantage of the process according to the present invention is that very cheap peroxyacetic acid is used for the oxidation. Another advantage of the process according to the present invention is that omeprazole is isolated from the organic phase after completion of the reaction, and the acetic acid formed from the peroxyacetic acid during the reaction remains in the aqueous phase. This waste aqueous phase contains no toxic components and can be liquidated in an easy and cheap way.

The principal advantage of the process according to the present invention is that the prepared omeprazole is of high purity and practically contains no initial substance as well as the hardly removable sulphone impurity, 5-methoxy-2-[[(4-metoxy-3,5-dimethyl-2-pyridinyl)-methyl]sulphonyl]-1H-benzimidazole.

The present invention will be further illustrated in practical embodiments, without being limited to them.

EXAMPLES OF CARRYING OUT THE INVENTION

Example No. 1

3,29 g (0,01 mol) of 5-methoxy-2-[(4-methoxy-3,5-dimethyl-2-pyridinyl)-methylthio]-1H-benzimidazole is dissolved in 50 ml of dichloromethane and pH is adjusted to 8,0–8,5 by adding water solution of sodium carbonate. Then, 3,46 g (0,01 mol) of peroxyacetic acid is added in drops at temperature of the reaction compound from 0° C. to 5° C., and pH is maintained by adding water solution of sodium carbonate between 8,0 to 8,5. The reaction mixture is stirred for 120 minutes. Afterwards, the dichloromethane layer is separated and scrubbed with water and brine, dried with sodium sulphate and densified on a vacuum evaporator till it is dry. The yield is 3,27 g (94,8%) of omeprazole.

Example No. 2

3,29 g (0,01 mol) of 5-methoxy-2-[(4-methoxy-3,5-dimethyl-2-pyridinyl)-methylthio]-1H-benzimidazole is dissolved in 50 ml of chloroform and pH is adjusted to 7,1–7,6 by adding water solution of sodium carbonate. Then, 2,76 g (0,008 mol) of peroxyacetic acid is added in drops at temperature of the reaction mixture from 20° C. to 25° C., and pH is maintained by adding water solution of sodium carbonate between 7,1 to 7,6. The reaction mixture is stirred for 120 minutes. Afterwards, the chloroform layer is separated and scrubbed with water and brine, dried with sodium sulphate and densified on a vacuum evaporator till it is dry. The yield is 2,58 g (74,8%) of omeprazole.

Example No. 3

3,29 g (0,01 mol) of 5-methoxy-2-[(4-methoxy-3,5-dimethyl-2-pyridinyl)-methylthio]-1H-benzimidazole is dissolved in 50 ml of dichloroethane and pH is adjusted to 9,0–9,5 by adding water solution of sodium carbonate. Then, 6,92 g (0,02 mol) of peroxyacetic acid is added in drops at temperature of the reaction mixture from 5° C. to 10° C., and pH is maintained by adding water solution of sodium carbonate between 9,0 to 9,5. The reaction mixture is stirred for 120 minutes. Afterwards, the dichloroethane layer is separated and scrubbed with water and brine, dried with sodium sulphate and densified on a vacuum evaporator till it is dry.

The yield is 2,76 g (80,1%) of omeprazole.

Example No. 4

3,29 g (0,01 mol) of 5-methoxy-2-[(4-methoxy-3,5-dimethyl-2-pyridinyl)-methylthio]-1H-benzimidazole is dissolved in 50 ml of dichloromethane and pH is adjusted to 8,0–8,5 by water solution of sodium carbonate. Then, 3,81 g (0,011 mol) of peroxyacetic acid is added in drops at temperature of the reaction mixture from 10° C. to 15° C., and pH is maintained by adding water solution of sodium carbonate between 8,0 to 8,5. The reaction mixture is stirred for 120 minutes. Afterwards, the dichloromethane layer is separated and scrubbed with water and brine, dried with sodium sulphate and densified on a vacuum evaporator till it is dry.

The yield is 3,15 g (90,2%) of omeprazole.

Industrial Utilisation

Omeprazole is used in pharmaceutical industry as a pharmaceutical substance in human medicine.

What is claimed is:

1. The method of omeprazole preparation characterised by reaction of 5-methoxy-2-[(4-methoxy-3,5-dimethyl-2-pyridinyl)-methylthio]-1H-benzimidazole with peroxyacetic acid in a two-phase water and chlorinated organic solvent medium, in pH ranging from 7.1 to 9.5, subsequent separation of water and organic phases after the reaction and isolation of omeprazole from organic phase.

2. The method according to claim 1, characterized by using 0.8 to 2.0 molar equivalents, of peroxyacetic acid to 5-methoxy-2-[(4-methoxy -3,5-dimethyl-2-pyridinyl)-methylthio]-1H-benzimidazole.

3. The method according to claim 1, characterised by maintaining the temperature of reaction mixture in the range from 0° C. to 25° C.

4. The method according to claim 1, characterised by using dichloromethane, chloroform or dichloroethane as chlorinated organic solvent.

5. The method according to claim 2, characterised by using 0.9 to 1.1 molar equivalent of peroxyacetic acid to 5-methoxy -2-[(4-methoxy-3,5-dimethyl-2-pyridinyl)-methylthio]-1H-benzimidazole.

6. The method according to claim 1, characterised by maintaining the alkaline pH of the reaction mixture in the range from 8.0 to 8.5.

7. The method according to claim 3, characterised by maintaining the temperature of reaction mixture in the range from 1° C. to 5° C.

8. The method according to claim 4, characterised by using dichlormethane as chlorinated organic solvent.

9. The method of omeprazole preparation characterised by reaction of 5-methoxy-2-[(4-methoxy-3,5-dimethyl-2-pyridinyl)-methylthio]-1H-benzimidazole with peroxyacetic acid in a two-phase water and chlorinated organic solvent medium, in pH ranging from 8.0 to 8.5, subsequent separation of water and organic phases after the reaction and isolation of omeprazole from organic phase.

* * * * *